(12) United States Patent
Quinn et al.

(10) Patent No.: US 12,318,145 B2
(45) Date of Patent: *Jun. 3, 2025

(54) DEPICTING FORCE

(71) Applicant: St. Jude Medical, Cardiology Division, Inc., St. Paul, MN (US)

(72) Inventors: Michael A. Quinn, St. Paul, MN (US); Daniel R. Starks, Lake Elmo, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1348 days.

This patent is subject to a terminal disclaimer.

(21) Appl. No.: 16/913,692

(22) Filed: Jun. 26, 2020

(65) Prior Publication Data

US 2020/0390504 A1 Dec. 17, 2020

Related U.S. Application Data

(62) Division of application No. 14/699,737, filed on Apr. 29, 2015, now Pat. No. 10,729,500.

(Continued)

(51) Int. Cl.
*A61B 34/20* (2016.01)
*A61B 5/00* (2006.01)
(Continued)

(52) U.S. Cl.
CPC .............. *A61B 34/20* (2016.02); *A61B 5/283* (2021.01); *A61B 5/6852* (2013.01);
(Continued)

(58) Field of Classification Search
CPC ... A61B 34/20; A61B 5/7445; A61B 18/1492; A61B 90/37; A61B 2090/064
See application file for complete search history.

(56) References Cited

U.S. PATENT DOCUMENTS

| D240,647 S | 7/1976 | Root |
| D243,320 S | 2/1977 | MacWilliams |

(Continued)

FOREIGN PATENT DOCUMENTS

| EP | 2248480 A1 | 11/2010 |
| EP | 2201890 B1 | 1/2013 |

(Continued)

OTHER PUBLICATIONS

Alternative to Open Heart Bypass Surgery at Sanford Health, posted at Medical-Horizons.net, posted May 9, 2013, Medical Horizon, available from the Internet: <http://www.medical-horizons.net/blog-view.php?id=70>.

(Continued)

*Primary Examiner* — May A Abouelela
*Assistant Examiner* — Yasmeen S Warsi
(74) *Attorney, Agent, or Firm* — Wiley Rein LLP

(57) ABSTRACT

A force exerted on a distal end of an elongate medical device can be determined. A graphical representation of the distal end of the elongate medical device and a graphical representation of the force exerted on the distal end of the elongate medical device can be computed. The graphical representation of the force can emanate from the graphical representation of the distal end of the elongate medical device. A first dimension of the graphical representation of the force can be increased in response to a longitudinal force being exerted on the distal end of the elongate medical device. A second dimension of the graphical representation of force can be increased in response to a lateral force being exerted on the distal end of the elongate medical device.

20 Claims, 7 Drawing Sheets

Related U.S. Application Data

(60) Provisional application No. 61/987,332, filed on May 1, 2014.

(51) Int. Cl.

| | | |
|---|---|---|
| *A61B 5/283* | (2021.01) | |
| *A61B 18/14* | (2006.01) | |
| *A61B 90/00* | (2016.01) | |
| *A61B 90/92* | (2016.01) | |
| *A61M 25/01* | (2006.01) | |
| *G06F 3/01* | (2006.01) | |
| *A61B 18/00* | (2006.01) | |

(52) U.S. Cl.
CPC .......... *A61B 5/6885* (2013.01); *A61B 5/7445* (2013.01); *A61B 18/1492* (2013.01); *A61B 90/06* (2016.02); *A61B 90/37* (2016.02); *A61B 90/92* (2016.02); *A61M 25/0105* (2013.01); *G06F 3/016* (2013.01); *A61B 2018/00577* (2013.01); *A61B 2018/00839* (2013.01); *A61B 2034/2046* (2016.02); *A61B 2090/064* (2016.02); *A61B 2090/065* (2016.02); *A61M 2025/0166* (2013.01)

(56) References Cited

U.S. PATENT DOCUMENTS

| | | |
|---|---|---|
| D359,545 S | 6/1995 | Canler |
| D362,402 S | 9/1995 | Hite |
| D372,308 S | 7/1996 | Stuart |
| D401,666 S | 11/1998 | Lee |
| D401,997 S | 12/1998 | Lee |
| D401,998 S | 12/1998 | Lee |
| D471,599 S | 3/2003 | Manville |
| D471,949 S | 3/2003 | Thomas |
| D517,123 S | 3/2006 | Sidwell |
| D520,576 S | 5/2006 | Sonnon et al. |
| D542,914 S | 5/2007 | Tanghoj |
| D550,356 S | 9/2007 | Anderson et al. |
| D552,733 S | 10/2007 | Criscuolo et al. |
| D558,086 S | 12/2007 | Herber |
| D562,411 S | 2/2008 | Jones |
| D572,772 S | 7/2008 | Barton |
| D575,353 S | 8/2008 | Barton |
| D577,391 S | 9/2008 | Barton |
| 7,511,703 B2 | 3/2009 | Wilson et al. |
| D603,044 S | 10/2009 | Appling et al. |
| D617,448 S | 6/2010 | Singh |
| D625,409 S | 10/2010 | Chesnin et al. |
| D626,648 S | 11/2010 | Ahlgren |
| D627,836 S | 11/2010 | Hanoun |
| D627,879 S | 11/2010 | Bruns |
| D628,659 S | 12/2010 | Burns |
| D630,321 S | 1/2011 | Hamilton, Jr. |
| D630,729 S | 1/2011 | Bierman |
| D630,733 S | 1/2011 | Ahlgren |
| D631,154 S | 1/2011 | Hamilton, Jr. |
| D640,767 S | 6/2011 | Renosky et al. |
| D648,851 S | 11/2011 | Copeland |
| D657,787 S | 4/2012 | Fletcher |
| D659,212 S | 5/2012 | Smith et al. |
| 8,206,380 B2 | 6/2012 | Lenihan et al. |
| D663,743 S | 7/2012 | Tanghe et al. |
| D663,744 S | 7/2012 | Tanghe et al. |
| D689,089 S | 9/2013 | Impas et al. |
| 8,532,738 B2 | 9/2013 | Zino |
| D699,745 S | 2/2014 | Pearson et al. |
| D700,318 S | 2/2014 | Amoah et al. |
| D704,330 S | 5/2014 | Cicatelli |
| D705,925 S | 5/2014 | Murray et al. |
| 8,849,382 B2 | 9/2014 | Cox et al. |
| 8,979,842 B2 | 3/2015 | McNall, III et al. |
| D727,437 S | 4/2015 | Padilla |
| 9,005,106 B2 | 4/2015 | Gross et al. |
| 9,113,843 B2 | 8/2015 | Manstrom et al. |
| D738,434 S | 9/2015 | Baumann |
| D738,960 S | 9/2015 | Padilla |
| D738,961 S | 9/2015 | Padilla |
| D739,472 S | 9/2015 | Padilla |
| D739,473 S | 9/2015 | Padilla |
| 9,125,600 B2 | 9/2015 | Steube et al. |
| 9,125,655 B2 | 9/2015 | Gharib et al. |
| 9,140,715 B2 | 9/2015 | Wilson et al. |
| 9,144,449 B2 | 9/2015 | Burr et al. |
| D741,901 S | 10/2015 | Gardner et al. |
| 9,152,829 B2 | 10/2015 | Day et al. |
| 9,186,063 B2 | 11/2015 | Goldman et al. |
| D748,137 S | 1/2016 | Merschon et al. |
| D753,150 S | 4/2016 | Chmiel et al. |
| 9,326,700 B2 | 5/2016 | Govan et al. |
| 2008/0091121 A1 | 4/2008 | Sun et al. |
| 2008/0294144 A1 | 11/2008 | Leo et al. |
| 2009/0177111 A1 | 7/2009 | Miller et al. |
| 2010/0160770 A1* | 6/2010 | Govari .................. A61B 5/062 600/407 |
| 2010/0169815 A1 | 7/2010 | Zhao et al. |
| 2010/0256624 A1 | 10/2010 | Brannan et al. |
| 2011/0144524 A1 | 6/2011 | Fish et al. |
| 2012/0157825 A1 | 6/2012 | Koyrakh et al. |
| 2012/0172713 A1 | 7/2012 | Carbonera et al. |
| 2012/0179070 A1 | 7/2012 | Pommer et al. |
| 2012/0237105 A1 | 9/2012 | Mielekamp |
| 2013/0226169 A1 | 8/2013 | Miller |
| 2014/0100484 A1 | 4/2014 | Tsusaka et al. |
| 2015/0112149 A1 | 4/2015 | Govari et al. |
| 2015/0313547 A1 | 11/2015 | Quinn et al. |

FOREIGN PATENT DOCUMENTS

| | | |
|---|---|---|
| JP | 2012133693 A | 7/2012 |
| WO | 2010147972 A1 | 12/2010 |

OTHER PUBLICATIONS

Filling That Hole in Your Heart, posted at Txchnologist.com by Boston Children's Hospital, posting date not posted, available from Internet: <http://txchnologist.com/post/131031123245/filling-that-hole-in-your-heart-repairing-defects>.

Heart Catheter, posted at Cat-Medic.com by Springer Medicine via Cat Production, posting date not posted, Cat Production GmbH, available from internet: <http://www.cat-medic.com/otw-portfolio/heart-catheter/>.

Medical Device Breakthrough, posted at PRNewsWire.com by Boston Children's Hospital, posted Oct. 5, 2015, PR Newswire Association LLC., Available from internet :<http://www.prnewswire.com/news-releasesimedical-devicebreakthrough-uv-light-enabled-catheter-fixes-holes-in-the-heart-without-invasive-surgery-300154020.html>.

Death Worm Gameplay. youtube.com [online]. Jul. 27, 2008. Retrieved from the Internet:<URL:https:www.youtube.corn/watch?v=IBSgw7XgRIU>.

Heart Catheterization Animation. WebMacom [online]. Jan. 23, 2014. Retrieved from the Internet<URL:http://www.webmd.com/heart-disease/videoicardiac-catheterization>.

Insulin pen instruction animation. youtube.com [online]. Sep. 16, 2011. Retrieved from the Internet<URL https://www.youtube.comlwatch?v=INo.8 JoL3g>.

Nerf Dart Greenscreen. youtube.com [online]. Jun. 10, 2013. Retrieved from the Internet: <URL:https://www.youtube.comfwatch?v=OTRBm0DtW4>.

Kwok et al., "MRI-based visual and haptic catheter feedback: simulating a novel system's contribution to efficient and safe MRI-guided cardiac electrophysiology procedures," Journal of Cardiovascular Magnetic Resonance (http://www.lcmr-online.com/content/16/S1/O50), Jan. 16, 2014, pp. 1-3.

Kesner, Samuel B. et al., "Discriminating Tissue Stiffness with a Haptic Catheter: Feeling the Inside of the Beating Heart," IEEE—World Haptics Conference 2011, Jun. 22-24, 2011, Istanbul, Turkey, pp. 1-6.

(56) References Cited

OTHER PUBLICATIONS

Biosense Webster, Inc., "ThermoCoolSmartTouch" Contact Force Sensing Catheter [Brochure]. (2011) (http://www.incathlab.com/files/12110_brochure_SmartTouch_Bdetpdf), n.p., n. pag.

* cited by examiner

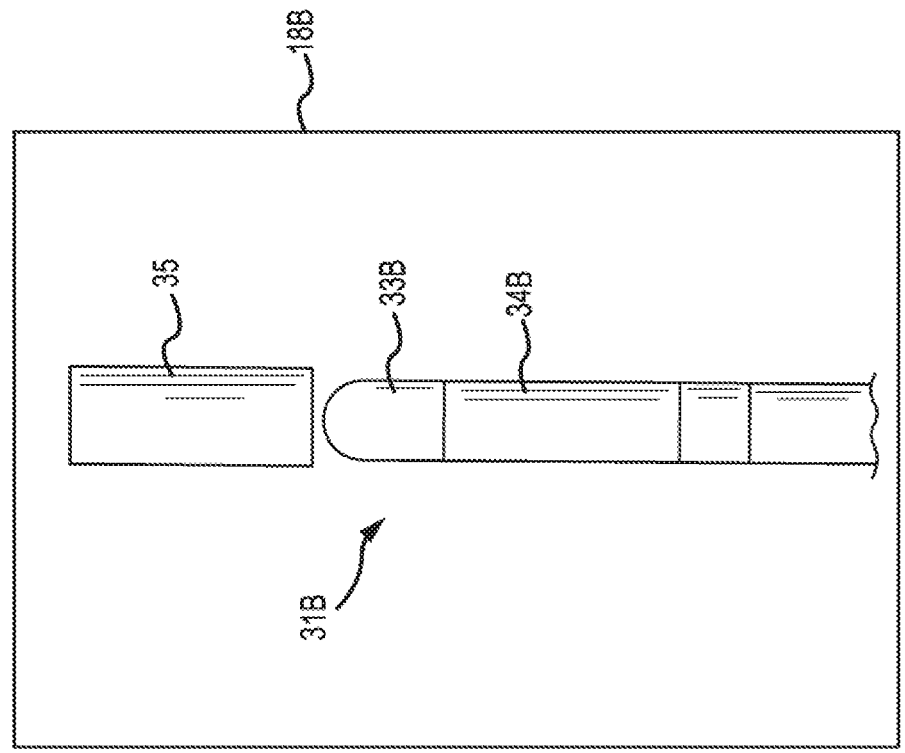
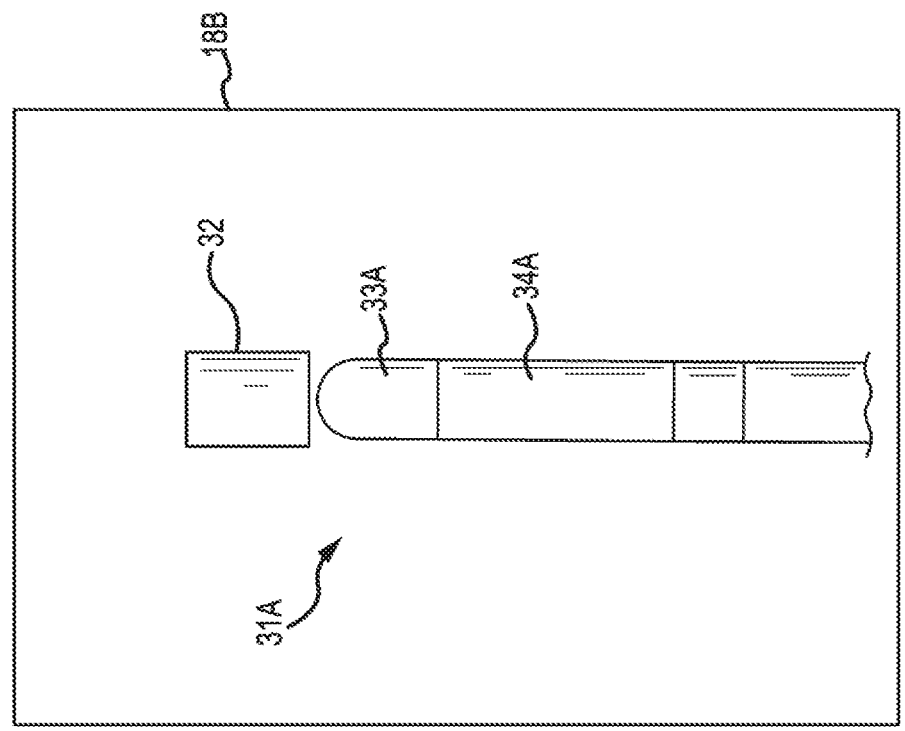

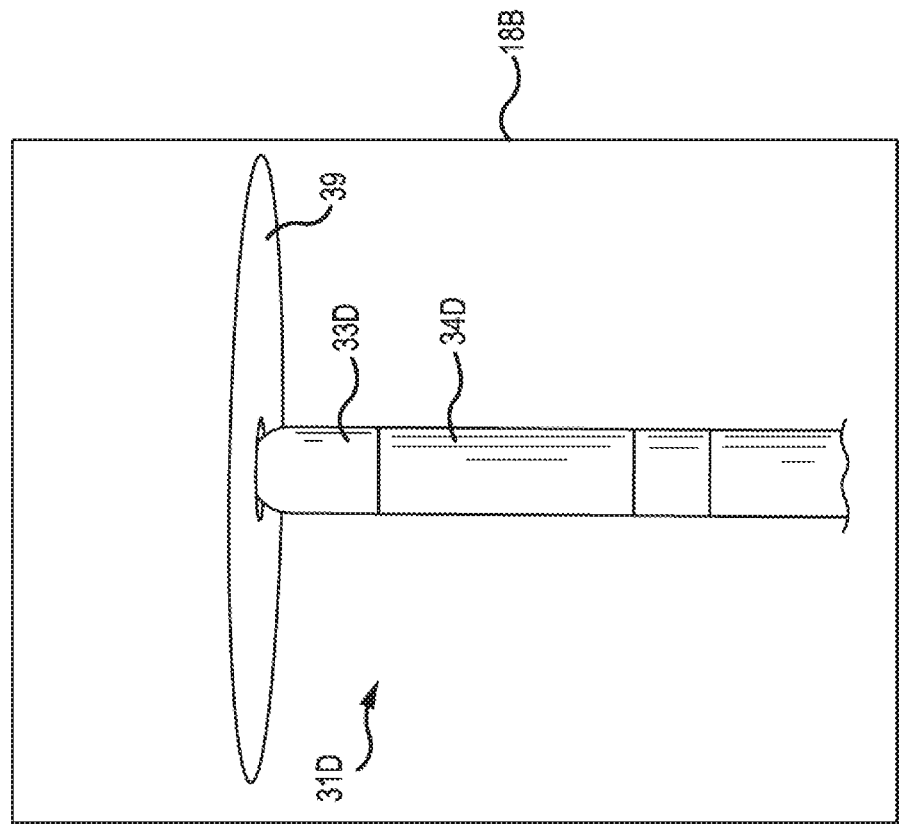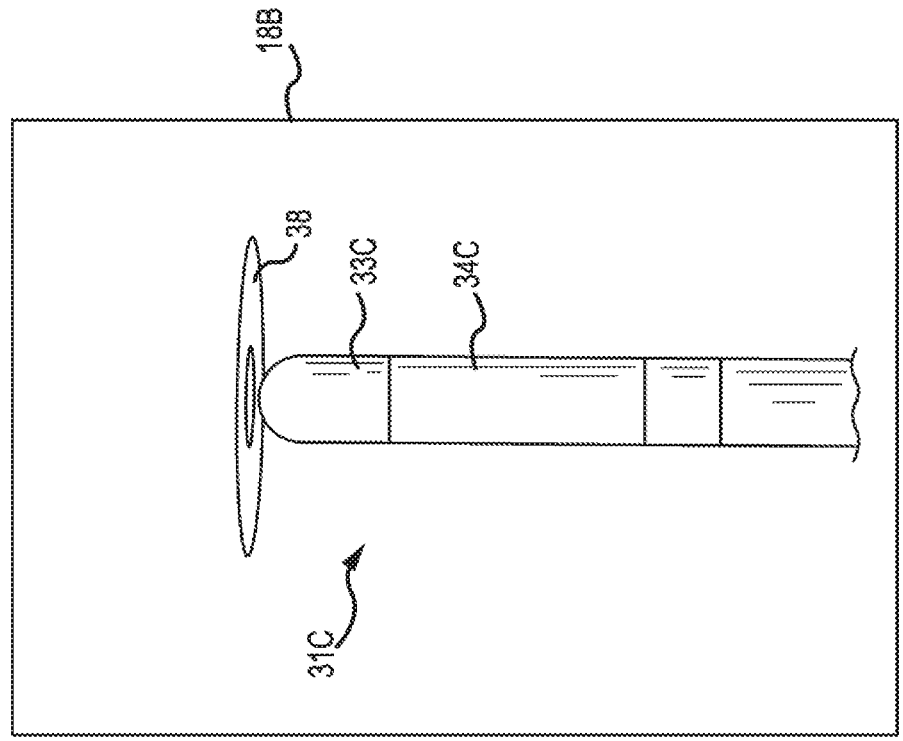

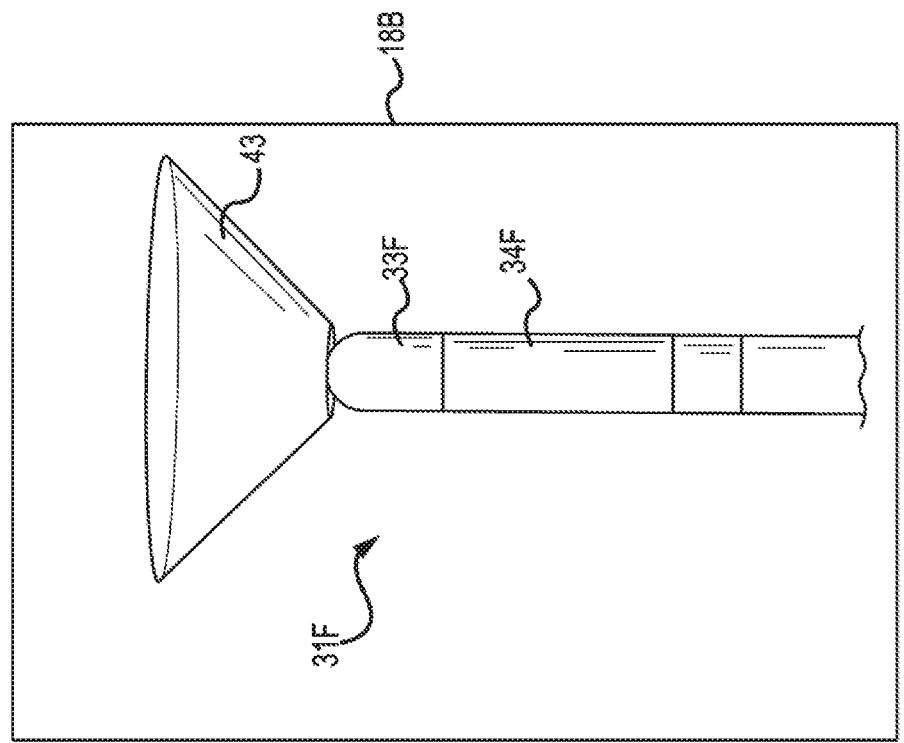
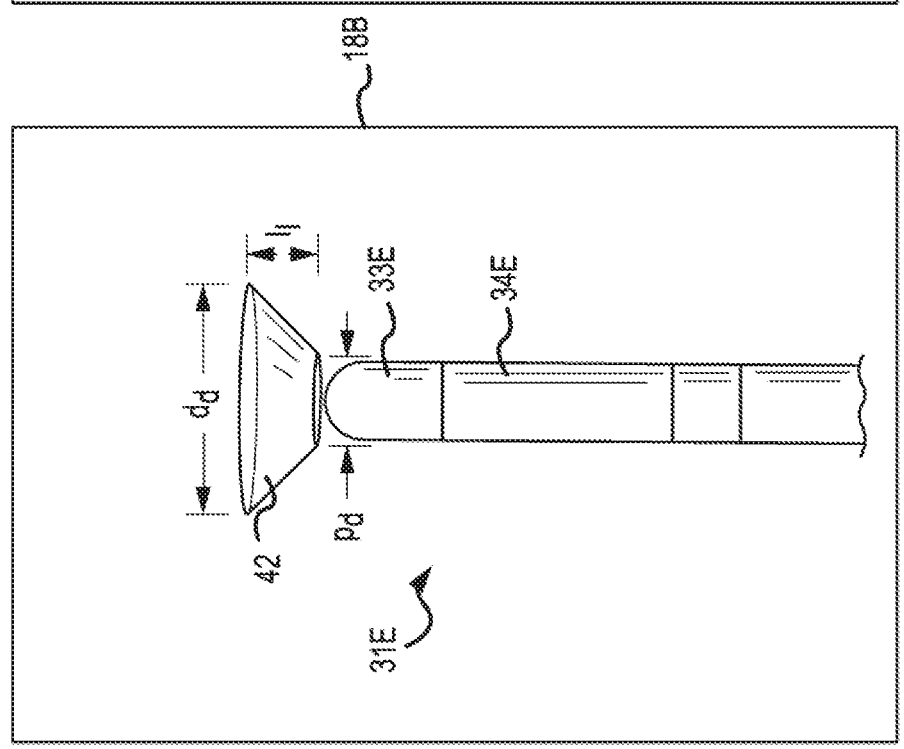

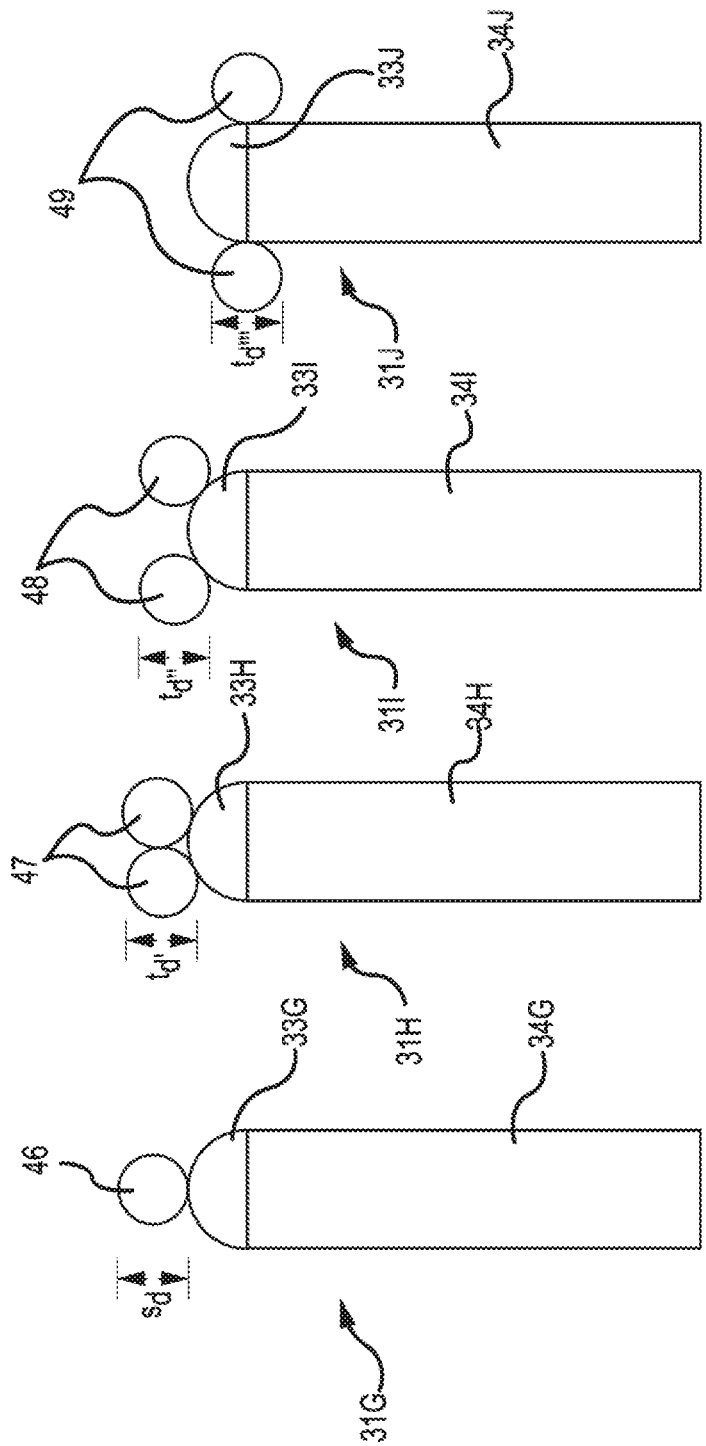

DEPICTING FORCE

CROSS-REFERENCE TO RELATED APPLICATIONS

This application is a United Stats divisional patent application of U.S. application Ser. No. 14/699,737, filed 29 Apr. 2015 (the '737 application), now issued as U.S. Pat. No. 10,729,500 on 4 Aug. 2020. This application claims priority to U.S. provisional patent application No. 61/987,332 (the '332 application), filed on 1 May 2014. This application is also related to United States design application Ser. No. 29/489,667 (the '667 application), filed on 1 May 2014, and United States design application Ser. No. 29/489,669 (the '669 application), filed on 1 May 2014. The '737 application, the '332 application, the '667 application, and the '669 application are hereby incorporated by reference as though fully set forth herein.

BACKGROUND a. Field of the Disclosure

This disclosure relates to depicting a force exerted on a distal end of an elongate medical device.

b. Background Art

Elongate medical devices (e.g., catheters) can be operatively connected to various types of sensors and active elements and can be used in a variety of diagnostic and/or therapeutic medical procedures. For example, electrodes can be used on cardiac mapping catheters to determine electric potentials in the heart. Likewise, catheters with electrodes or magnetic coils can be used to generate an image of the internal geometry of a heart, and can be used (separately or in combination) to match the electrical potentials with a location on the tissue. Electrodes and other active elements can also be used on ablation catheters to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions, and stasis of blood flow, which can lead to a variety of ailments and even death. It is believed that the primary cause of atrial arrhythmia is stray electrical signals within the left or right atrium of the heart. The ablation catheter imparts ablative energy (radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

In some diagnostic and/or therapeutic medical procedures, a catheter is inserted into a chamber of the heart and brought into contact with the inner heart wall. In such procedures, it can be important that the distal tip of the catheter engages the endocardium and/or engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. As discussed herein, the electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without causing damage to the tissue and/or perforation of the heart wall.

SUMMARY

In various embodiments, instructions are executable by a processing resource to determine a force exerted on a distal end of an elongate medical device. The determination can include a determination of an amount of longitudinal force exerted on the distal end of the elongate medical device and an amount of lateral force exerted on the distal end of the elongate medical device. A graphical representation of the distal end of the elongate medical device and a graphical representation of the force exerted on the distal end of the elongate medical device can be computed. The graphical representation of the force emanates from the graphical representation of the distal end of the elongate medical device. A first dimension of the graphical representation of the force can be increased in response to a longitudinal force being exerted on the distal end of the elongate medical device and a second dimension of the graphical representation of force can be increased in response to a lateral force being exerted on the distal end of the elongate medical device. In some embodiments, an indicator shape that is representative of the force exerted on the distal end of the elongate medical device can be displayed. A first dimension of the indicator shape can be increased or decreased in response to a change in the amount of longitudinal force being exerted on the distal end of the elongate medical device and a second dimension of the indicator shape can be increased or decreased in response to a change in the amount of lateral force being exerted on the distal end of the elongate medical device. The graphical representation of the longitudinal force can be displayed as a cylinder that extends from a distal end of the graphical representation of the elongate medical device and along a longitudinal axis defined by the elongate medical device. In some embodiments, the graphical representation of the amount of longitudinal force can be displayed as the cylinder, in response to the amount of longitudinal force exceeding a defined amount of longitudinal force and an amount of lateral force being less than a defined amount of lateral force. A longitudinal length of the cylinder can be changed in response to a change in the longitudinal force exerted on the distal end of the elongate medical device. The graphical representation of the lateral force can be displayed as a disk that emanates from the graphical representation of the distal end of the elongate medical device. In some embodiments, the graphical representation of the amount of lateral force can be displayed as the disk, in response to the amount of the lateral force exceeding a defined amount of lateral force and an amount of longitudinal force being less than a defined amount of longitudinal force. A diameter of the disk can be changed in response to a change in the lateral force exerted on the distal end of the elongate medical device. In some embodiments, a color of the indicator shape can be changed from a first color to a second color in response to an amount of the force exerted on the distal end of the elongate medical device exceeding a threshold.

In various embodiments, a method is provided for depicting force. The method can include determining a force exerted on a distal end of an elongate medical device. An amount of longitudinal force exerted on the distal end of the elongate medical device and an amount of lateral force exerted on the distal end of the elongate medical device can be determined. The method can include computing, with a computing device, a graphical representation of the force exerted on the distal end of the elongate medical device. The graphical representation of the force can be a first type of indicator shape for a pure longitudinal force exerted on the distal end of the elongate medical device and a second type of indicator shape for a pure lateral force exerted on the distal end of the elongate medical device. In various embodiments, the first type of indicator shape can be a sphere located at a distal tip of the distal end of the elongate medical device and the second type of indicator shape can be a torus located proximally from the distal tip of the distal end of the elongate medical device and can be coaxial with the distal end of the elongate medical device. In various embodiments, the first type of indicator shape can be a cylinder that extends from a distal end of the elongate medical device along an axis defined by the elongate medical device and the second type of indicator shape can be a disk. In some embodiments, a length of the cylinder can be increased in response to an increasing amount of longitudinal force being exerted on the distal end of the elongate medical device. In some embodiments, a diameter of the disk can be increased in response to an increasing amount of lateral force being exerted on the distal end of the elongate medical device. The method can include displaying the graphical representation of the force exerted on the distal end of the elongate medical device next to a graphical representation of a distal end of the elongate medical device. The first type of indicator shape can be merged with the second type of indicator shape in response to both longitudinal force and lateral force being exerted on the distal end of the elongate medical device. In some embodiments, the first type of indicator shape can be transformed into the second type of indicator shape as the amount of longitudinal force decreases and the amount of lateral force increases. In some embodiments, the second type of indicator shape can be transformed into the first type of indicator shape as the amount of longitudinal force increases and the amount of lateral force decreases.

In various embodiments, a system for force imaging is provided to determine an amount of longitudinal force and an amount of lateral force exerted on a distal end of an elongate medical device. A graphical representation of the amount of longitudinal force and the amount of lateral force can be displayed via an indicator shape next to a distal end of a graphical representation of the distal end of the elongate medical device. The indicator shape can have a fixed proximal diameter, a variable distal diameter, and a variable length between the fixed proximal diameter and the variable distal diameter along an axis of the elongate medical device. In response to a change in the amount of longitudinal force being exerted on the distal end of the elongate medical device, the variable length between the fixed proximal diameter and the variable distal diameter can be changed. In response to a pure lateral force being exerted on the distal end of the elongate medical device, the length between the fixed proximal diameter and the variable distal diameter can be zero. In response to a change in the amount of lateral force being exerted on the distal end of the elongate medical device, the variable distal diameter can be changed. In response to a pure longitudinal force being exerted on the distal end of the elongate medical device, the fixed proximal diameter and the variable distal diameter can be a same diameter. In some embodiments, the indicator shape can be displayed as a cylinder in response to exertion of a pure longitudinal force being exerted on the distal end of the elongate medical device. In some embodiments, the indicator shape can be displayed as a disk in response to a pure lateral force being exerted on the distal end of the elongate medical device.

BRIEF DESCRIPTION OF THE DRAWINGS

FIGS. 2A and 2B illustrate a graphical representation of a distal end of an elongate medical device and longitudinal force exerted on the distal end of the elongate medical device.

FIGS. 3A and 3B illustrate a graphical representation of a distal end of an elongate medical device and lateral force exerted on the distal end of the elongate medical device.

FIGS. 4A and 4B illustrate a graphical representation of a distal end of an elongate medical device and mixed lateral and longitudinal forces exerted on the distal end of the elongate medical device.

FIGS. 5A-5D illustrate an alternate embodiment of a graphical representation of force exerted on a distal end of an elongate medical device.

DETAILED DESCRIPTION

Figure 1:
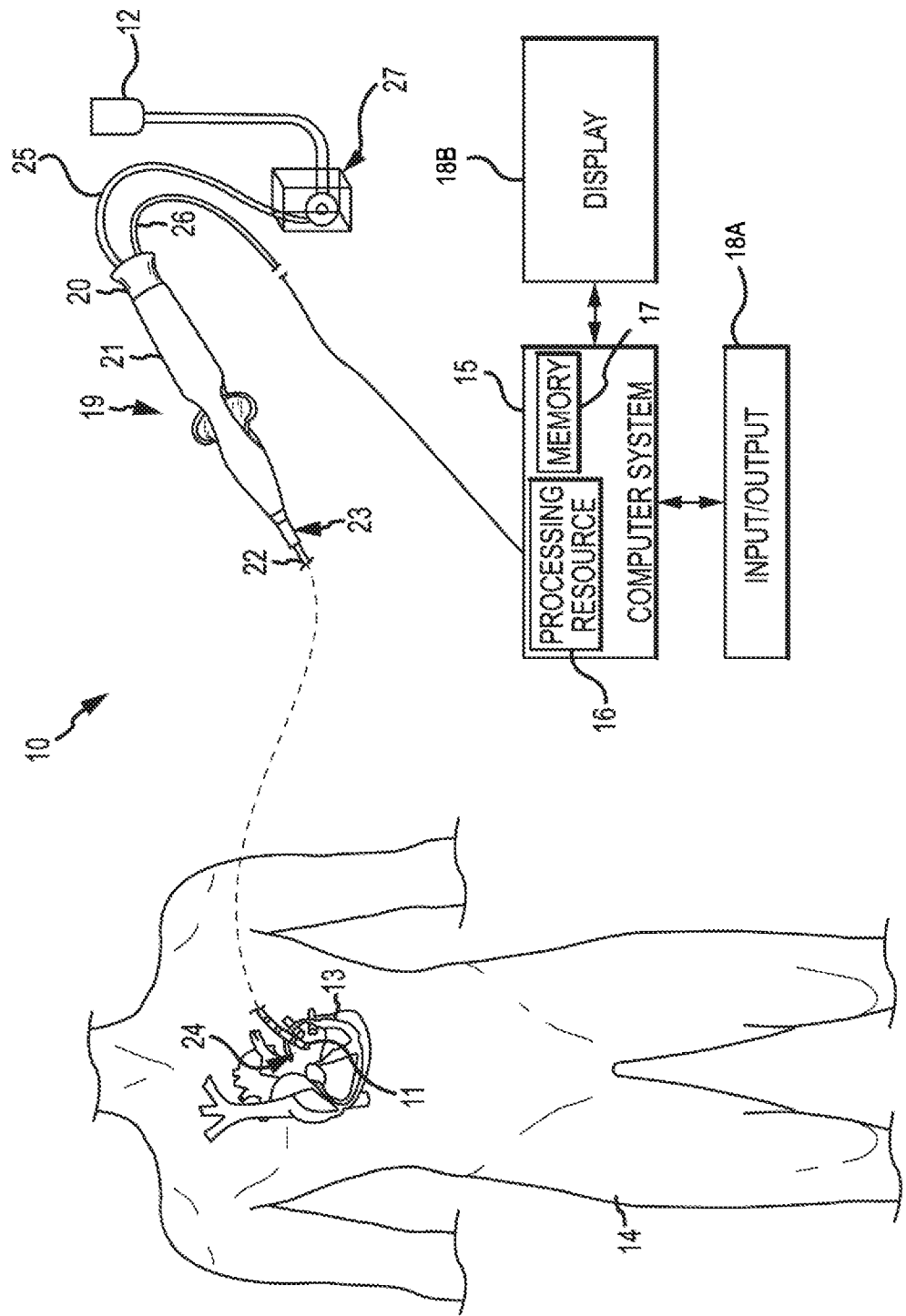
FIG. 1 is a diagrammatic overview of a system for force imaging, in accordance with embodiments of the present disclosure.

Referring now to the drawings wherein like reference numerals are used to identify identical components in the various views, FIG. 1 generally illustrates a system 10 for force imaging having an elongate medical device 19 that includes an electrode assembly 11 configured to be used in the body for medical procedures. The electrode assembly 11 is included as part of a medical device such as an elongate medical device 19 and may be used for diagnosis, visualization, and/or treatment of tissue 13 (such as cardiac or other tissue) in the body. For example, the electrode assembly 11 may be used for ablation therapy of tissue 13 or mapping purposes in a patient's body 14. FIG. 1 further shows various sub-systems included in the overall system 10. The system 10 may include a main computer system 15 (including an electronic control unit 16 and data storage 17, e.g., memory). The computer system 15 may further include conventional interface components, such as various user input/output mechanisms 18A and a display 18B, among other components. Information provided by the electrode assembly 11 may be processed by the computer system 15 and may provide data to the clinician via the input/output mechanisms 18A and/or the display 18B, or in other ways as described herein.

In the illustrative embodiment, the elongate medical device 19 may include a cable connector or interface 20, a handle 21, a tubular body or shaft 22 having a proximal end 23 and a distal end 24. The elongate medical device 19 may also include other conventional components not illustrated herein, such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the elongate medical device 19.

The handle 21 provides a portion for a user to grasp or hold the elongate medical device 19 and may further provide a mechanism for steering or guiding the shaft 22 within the patient's body 14. For example, the handle 21 may include a mechanism configured to change the tension on a pull-wire extending through the elongate medical device 19 to the distal end 24 of the shaft 22 or some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the electrode assembly 11. For example, if contact to tissue 13 is made by the electrode assembly 11, the handle 21 may include light-emitting-diodes, a tone generator, a vibrating mechanical transducer, and/or other indicator(s), the outputs of which could vary in proportion to the signal sensed at the electrode assembly.

The computer system 15 can utilize software, hardware, firmware, and/or logic to perform a number of functions described herein. The computer system 15 can be a combination of hardware and instructions to share information. The hardware, for example can include processing resource 16 and/or a memory 17 (e.g., non-transitory computer-readable medium (CRM) database, etc.). A processing resource 16, as used herein, can include a number of processors capable of executing instructions stored by the memory resource 17. Processing resource 16 can be integrated in a single device or distributed across multiple devices. The instructions (e.g., computer-readable instructions (CRI)) can include instructions stored on the memory 17 and executable by the processing resource 16 for force imaging.

The memory resource 33 can be in communication with the processing resource 32. A memory 17, as used herein, can include a number of memory components capable of storing instructions that can be executed by processing resource 16. Such a memory 17 can be a non-transitory CRM. The memory 17 can be integrated in a single device or distributed across multiple devices. Further, the memory 17 can be fully or partially integrated in the same device as the processing resource 16 or it can be separate but accessible to that device and the processing resource 16. Thus, it is noted that the computer system 15 can be implemented on a user device and/or a collection of user devices, on a mobile device and/or a collection of mobile devices, and/or on a combination of the user devices and the mobile devices.

The memory 17 can be in communication with the processing resource 16 via a communication link (e.g., path). The communication link can be local or remote to a computing device associated with the processing resource 16. Examples of a local communication link can include an electronic bus internal to a computing device where the memory 17 is one of a volatile, non-volatile, fixed, and/or removable storage medium in communication with the processing resource 16 via the electronic bus.

Referring to FIGS. 2A and 2B, a graphical representation of a distal end of an elongate medical device and longitudinal force exerted on the distal end of the elongate medical device is generally illustrated. With reference to FIG. 2A, the graphical representation of the elongate medical device 31A can include an elongate shaft 34A (e.g., catheter shaft) and a distal end 33A (e.g., electrode tip). The graphical representation of the elongate medical device 31A can be displayed on a display 18B, which can be a graphical user interface (GUI).

In some embodiments, an orientation of the graphical representation of the elongate medical device 31A can be correlated with an orientation of an elongate medical device 19 that has been inserted into a patient's body 14. For example, an electrode can be placed within an elongate shaft and/or distal end of the elongate medical device 19. In addition, patch electrodes (e.g., X-axis electrode, Y-axis patch electrode, Z-axis electrode) can be attached to a patient, which can obtain raw patch data (i.e., voltage readings) from a signal produced by the electrode placed within the elongate shaft and/or physical distal end. The raw patch data can be used to determine raw electrode location coordinates in three-dimensional space (X,Y,Z) of the electrode placed within the elongate shaft and/or distal end of the elongate medical device 19. The raw electrode location coordinates can be used to construct a graphical representation of the elongate medical device 31A to display an orientation and/or position of the elongate medical device 19 on the display 18B.

Some embodiments of the present disclosure can include depicting a force exerted on a distal end of the elongate medical device 19. As discussed herein, in some diagnostic and/or therapeutic medical procedures, an elongate medical device 19 can be inserted into a chamber of the heart and brought into contact with the inner heart wall. In medical procedures, such as ablation, it can be important for the distal tip of the elongate medical device to engage the endocardium and/or engage the endocardium with sufficient pressure to ensure that a good lesion is formed by an electrode attached to the distal tip. Excessive pressure, however, may cause undesired damage to the heart tissue and even perforation of the heart wall. Alternatively, not enough pressure may cause edema and/or may not sufficiently ablate the heart tissue at the site to create a good lesion.

It can therefore be beneficial to convey information associated with a force exerted on a distal end of the elongate medical device 19 to a physician to avoid complications associated with too much and/or too little pressure being applied between the heart tissue and the distal end of the elongate medical device 19. Accordingly, embodiments of the present disclosure can determine the force exerted on the distal end of the elongate medical device 19 and display a graphical representation of the longitudinal force 32. In some embodiments, the force exerted on the distal end of the elongate medical device 19 can be determined using various methods. One such method can use optical strain sensors to resolve the magnitude and direction of force being exerted on the distal end of the elongate medical device 19. In addition, methods can use piezoelectric sensors and/or strain gauges to resolve the magnitude and direction of force being exerted on the distal end of the elongate medical device 19.

The computer system 15, as discussed in relation to FIG. 1, can be in communication with the sensors and/or strain gauges and can receive information from the sensors and/or strain gauges to compute a magnitude of the force in the lateral and longitudinal directions relative to the distal end of the elongate medical device 19. The computer system 15 can use the computed magnitude of force in the lateral and longitudinal directions to determine a composite force vector acting on the distal end of the elongate medical device 19.

The computer system 15 can use the raw electrode location coordinates to compute a graphical representation of the elongate medical device 31A, including a graphical representation of the distal end of the elongate medical device 33A. In addition, the computer system 15 can use the composite force vector to compute a graphical representation of the longitudinal force 32 exerted on the distal end of the elongate medical device 19. The graphical representation of longitudinal force 32 can correspond with an amount (e.g., magnitude) of lateral and/or longitudinal force applied to the distal end of the elongate medical device 19. As used herein, lateral force can be defined as a force that is applied to a side of the distal end of the elongate medical device 19, and in some embodiments can include an angular force. As used herein, longitudinal force can be defined as a force that is applied to the distal end of the elongate medical device 19 along a direction parallel to a longitudinal axis defined by an elongate shaft and the distal end of the elongate medical device 19.

In some embodiments, the graphical representation of longitudinal force 32 can be displayed as an indicator shape. For instance, in FIG. 2A, the graphical representation of longitudinal force 32 is displayed as a cylinder along a longitudinal axis defined by the elongate medical device 19, which can be indicative of a pure longitudinal force being applied to the distal end of the elongate medical device 19. In response to a change (e.g., increase, decrease) in the amount of longitudinal force being exerted on the distal end of the elongate medical device 19, a first dimension of the indicator shape can be changed (e.g., increased, decreased). For example, in response to an amount of longitudinal force exerted on the distal end of the elongate medical device 19 being increased, a longitudinal length of the graphical representation of longitudinal force 32 (e.g., indicator shape) can increase, as shown in FIG. 2B by the graphical representation of increased longitudinal force 35.

FIG. 2B illustrates a graphical representation of the elongate medical device 31B that includes an elongate shaft 34B (e.g., catheter shaft) and a distal end 33B (e.g., electrode tip). In contrast to FIG. 2A, a first dimension (longitudinal length) of the graphical representation of longitudinal force 32 has been increased to indicate that an increased amount of longitudinal force is being exerted on the distal end of the elongate medical device 19. For instance, whereas the graphical representation of longitudinal force 32 may be representative of 10 grams of force being applied to the distal end of the elongate medical device 19, the graphical representation of increased longitudinal force 35 may be representative of 25 grams of force being applied to the distal end of the elongate medical device 19. Accordingly, as a physician watches the graphical representation of the elongate medical device 31A, 31B in relation to tissue 13, for example, the physician can be provided with a graphical representation of longitudinal force 32 and/or graphical representation of increased longitudinal force 35, without having to look at a different area of the display 18B.

In some embodiments, the length of the graphical representation of longitudinal force 32 (e.g., the indicator shape) can decrease as the amount of longitudinal force exerted on the distal end of the elongate medical device 19 decreases. In some embodiments, the length can decrease to zero, such that the graphical representation of longitudinal force 32 is not displayed. Alternatively, the length can decrease to a defined amount such that the indicator shape is still visible. For example, the length can be decreased to a defined number of pixels on the display 18B.

In some embodiments, the graphical representation of the amount of longitudinal force 32 can be displayed as the cylinder, in response to the amount of longitudinal force exceeding a defined amount of longitudinal force and an amount of lateral force being less than a defined amount of lateral force. In an example, a cut-off point can be established where the graphical representation of the amount of longitudinal force 32 is not displayed in response to the amount of longitudinal force being below the defined amount. Alternatively, the graphical representation of the amount of longitudinal force 32 can be displayed in response to the amount of longitudinal force being above the defined amount. In addition, the graphical representation of the amount of longitudinal force 32 can be displayed in response to the amount of lateral force being less than the defined amount of lateral force. As such, the graphical representation of the amount of longitudinal force 32 can be displayed as the cylinder, even though an amount (e.g., below a defined amount) of lateral force is being applied to the distal end of the elongate medical device 19.

Referring to FIGS. 3A and 3B, a graphical representation of a distal end of an elongate medical device and lateral force exerted on the distal end of the elongate medical device is generally illustrated. FIG. 3A includes a graphical representation of an elongate medical device 31C that includes a graphical representation of a distal end 33C and elongate shaft 34C displayed on display 18B. In contrast to FIGS. 2A and 2B, FIG. 3A displays a graphical representation of lateral force 38. The graphical representation of lateral force 38 can be displayed as an indicator shape, such as a disk.

In some embodiments, a second dimension of the graphical representation of force can be increased in response to a lateral force being exerted on the distal end of the elongate medical device 19. In response to a pure lateral force being exerted on the distal end of the elongate medical device 19, the length of the graphical representation of the longitudinal force can decrease to zero, such that the graphical representation of longitudinal force 32 is not displayed. Alternatively, the length of the graphical representation of longitudinal force can decrease to a defined amount such that the graphical representation of longitudinal force 32 is still visible. In response to a change (e.g., increase, decrease) in lateral force being exerted on the distal end of the elongate medical device 19, a second dimension of the indicator shape can be changed (e.g., increased, decreased). In some examples, the graphical representation of lateral force 38 can be displayed as a disk and a diameter of the disk can be changed in response to a change in the lateral force exerted on the distal end of the elongate medical device 19.

FIG. 3B illustrates a graphical representation of the elongate medical device 31D that includes an elongate shaft 34D (e.g., catheter shaft) and a distal end 33D (e.g., electrode tip) and a graphical representation of increased lateral force 39. In contrast to FIG. 3A, a first dimension of the graphical representation of lateral force 38 has been increased to indicate that an increased amount of lateral force is being exerted on the distal end of the elongate medical device 19. For instance, whereas the graphical representation of lateral force 38 may be representative of 10 grams of force being applied to the side of the distal end of the elongate medical device 19, the graphical representation of increased lateral force 39 may be representative of 25 grams of force being applied to the side of the distal end of the elongate medical device 19 (e.g., applied laterally with respect to the distal end of the elongate medical device 19).

In some embodiments, the diameter of the graphical representation of lateral force 38 (e.g., the indicator shape) can decrease as the amount of lateral force exerted on the side of the distal end of the elongate medical device 19 decreases. In some embodiments, the diameter can decrease to zero, such that the graphical representation of longitudinal force 38 is not displayed. Alternatively, the diameter can decrease to a defined amount such that the indicator shape is still visible. For example, the diameter can be decreased to a defined number of pixels on the display 18B.

In some embodiments, the graphical representation of the amount of lateral force 38 can be displayed as the disk, in response to the amount of lateral force exceeding a defined amount of lateral force and an amount of longitudinal force being less than a defined amount of longitudinal force. In an example, a cut-off point can be established where the graphical representation of the amount of lateral force 38 is not displayed in response to the amount of lateral force being below the defined amount. Alternatively, the graphical representation of the amount of lateral force 38 is displayed in response to the amount of lateral force being above the defined amount. In addition, the graphical representation of the amount of lateral force 38 can be displayed in response to the amount of lateral force being less than the defined amount of lateral force. As such, the graphical representation of the amount of lateral force 38 can be displayed as the disk even though an amount (e.g., below a defined amount) of longitudinal force is being applied to the distal end of the elongate medical device 19.

Referring to FIGS. 4A and 4B, a graphical representation of a distal end of an elongate medical device and mixed lateral and longitudinal forces exerted on the distal end of the elongate medical device is generally illustrated. FIG. 4A includes a graphical representation of an elongate medical device 31E that includes a graphical representation of a distal end 33E and elongate shaft 34E displayed on display 18B. In contrast to FIGS. 2A-3B, FIG. 4A displays a graphical representation of mixed lateral and longitudinal force 42 being applied to the distal end of the elongate medical device 19.

In some embodiments, a graphical representation of the mixed lateral and longitudinal force exerted on the distal end of the elongate medical device 19 can be computed. The graphical representation of the force can include a first type of indicator shape for a pure longitudinal force exerted on the distal end of the elongate medical device 19 and a second type of indicator shape for a pure lateral force exerted on the distal end of the elongate medical device 19. In an example, the first type of indicator shape can be a cylinder for the pure longitudinal force and the second type of indicator shape can be a disk for the pure lateral force, as discussed herein.

In some embodiments, in response to the mixed lateral and longitudinal forces being exerted on the distal end of the elongate medical device 19, the first type of indicator shape can be merged with the second type of indicator shape. For example, as an amount of longitudinal force exerted on the distal end of the elongate medical device 19 decreases and the amount of lateral force exerted on the distal end of the elongate medical device 19 increases, the cylinder representative of the longitudinal force can be transformed into the disk representative of the lateral force. Alternatively, as an amount of lateral force exerted on the distal end of the elongate medical device 19 decreases and the amount of longitudinal force exerted on the distal end of the elongate medical device 19 increases, the disk representative of the lateral force can be transformed into the cylinder representative of the longitudinal force.

For example, with reference to FIG. 4A, in response to an increase in lateral force from zero force and exertion of some amount of longitudinal force, a distal diameter ($d_d$) of the cylinder that is representative of the lateral force can be increased, while keeping a proximal diameter ($p_d$) fixed. As such, a frustoconical shape (e.g., graphical representation of mixed lateral and longitudinal force 42) can be formed, where $d_d$ is representative of an amount of lateral force applied to the distal end of the elongate medical device 19 and a longitudinal length ($l_l$) between the distal face and the proximal face of the frustoconical shape is representative of an amount of longitudinal force applied to the distal end of the elongate medical device 19. Accordingly, as an amount of longitudinal force exerted on the distal end of the elongate medical device 19 decreases and the amount of lateral force exerted on the distal end of the elongate medical device 19 increases, $d_d$ can increase and $l_l$ can decrease, until a disk is formed by a distal face of the frustoconical shape.

Alternatively, in response to an increase in longitudinal force from zero force and exertion of some amount of lateral force, $l_l$ between the distal face and proximal face of the frustoconical shape (e.g., which is zero at zero force, thus forming the disk) can be increased while keeping pa fixed. As such, a frustoconical shape (e.g., graphical representation of mixed lateral and longitudinal force 42) can be formed, where $d_d$ is representative of the amount of lateral force applied to the distal end of the elongate medical device 19 and $l_l$ representative of the amount of longitudinal force applied to the distal end of the elongate medical device 19. Accordingly, as an amount of longitudinal force exerted on the distal end of the elongate medical device 19 increases and the amount of lateral force exerted on the distal end of the elongate medical device 19 decreases, $d_d$ can decrease to a minimum diameter that is equal to the fixed $p_d$ and $l_l$ can increase, until a cylinder is formed.

FIG. 4B illustrates a graphical representation of an elongate medical device 31F that includes a graphical representation of a distal end 33F and elongate shaft 34F displayed on display 18B. In contrast, FIG. 4B displays a graphical representation of mixed lateral and longitudinal force 43 of an increased magnitude over mixed lateral and longitudinal force 42 in FIG. 4A.

Referring to FIGS. 5A-5D, an alternate embodiment of a graphical representation of force exerted on a distal end of an elongate medical device is generally illustrated. As shown in FIG. 5A, the graphical representation of the elongate medical device 31G includes a graphical representation of the distal tip 33G and a graphical representation of the elongate shaft 34G. In some embodiments, the first type of indicator shape can be a sphere 46 located at a distal tip of the graphical representation of the distal tip 33G. In an example, the diameter ($s_d$) of the sphere 46 can be representative of an amount of lateral force applied to the distal end of the elongate medical device 19. For instance, as the lateral force applied to the distal end of the elongate medical device 19 increases, $s_d$ can increase, thus increasing a size of the sphere 46.

As shown in FIG. 5B, the graphical representation of the elongate medical device 31H includes a graphical representation of the distal tip 33H and a graphical representation of the elongate shaft 34H. In some embodiments, the second type of indicator shape can be a torus 47. In an example, the position of the torus 47 along a longitudinal axis defined by the graphical representation of the elongate medical device 31H can be representative of an amount of longitudinal force applied to the distal end of the elongate medical device 19. For instance, as shown in FIG. 5C, the graphical representation of the elongate medical device 31I includes a graphical representation of the distal tip 33I and a graphical representation of the elongate shaft 34I. The torus 48 has been moved proximally along the longitudinal axis defined by the graphical representation of the elongate medical device 31I. In some embodiments, moving the torus 48 proximally along the longitudinal axis can be representative of an increase in longitudinal force being applied to the distal end of the elongate medical device 19.

As shown in FIG. 5D, the graphical representation of the elongate medical device 31J includes a graphical representation of the distal tip 33J and a graphical representation of the elongate shaft 34J. The torus 49 has been moved proximally further along the longitudinal axis defined by the graphical representation of the elongate medical device 31J, indicating that an increase in longitudinal force has been applied to the distal end of the elongate medical device 19. In some embodiments, the torus 49 can be coaxial with the graphical representation of the elongate medical device 31J, as the torus 49 moves proximally along the longitudinal axis defined by the graphical representation of the elongate medical device 31J. For example, the graphical representation of the elongate medical device 31J can push through a center of the torus 49, as the torus 49 moves proximally along the elongate medical device 31J.

As discussed herein, $s_d$ can be representative of an amount of lateral force applied to the distal end of the elongate medical device 19. As the lateral force applied to the distal end of the elongate medical device 19 increases, $s_d$ can increase, thus increasing a size of the sphere 46. In some embodiments, $s_d$ can be equivalent to a diameter $t_d$, $t_{d'}$, $t_{d''}$ of each torus 47, 48, 49, respectively. As such, $t_d$, $t_{d'}$, $t_{d''}$ can represent an amount of lateral force applied to the distal end of the elongate medical device 19. Accordingly, in response to an increase in the amount of lateral force applied to the distal end of the elongate medical device 19, $s_d$, $t_d$, $t_{d'}$, $t_{d''}$ can be increased. Alternatively, in response to a decrease in the amount of lateral force applied to the distal end of the elongate medical device 19, $s_d$, $t_d$, $t_{d'}$, $t_{d''}$ can be decreased.

In an example, $s_d$ can have a minimum size, such that when no lateral force is present, the sphere 46 is still visible. Accordingly, $t_d$, $t_{d'}$, $t_{d''}$ can have a minimum size that is equivalent to $s_d$, such that when no lateral force is present, toruses 47, 48, 49 are still visible.

In some embodiments, as discussed herein, the first type of indicator shape (e.g., sphere) can be merged with the second type of indicator shape (e.g., torus) in response to both longitudinal and lateral force being exerted on the distal end of the elongate medical device 19. For example, as an amount of longitudinal force exerted on the distal end of the elongate medical device 19 decreases and the amount of lateral force exerted on the distal end of the elongate medical device 19 increases, the torus representative of the longitudinal force can be transformed into the sphere representative of the lateral force. Alternatively, as an amount of lateral force exerted on the distal end of the elongate medical device 19 decreases and the amount of longitudinal force exerted on the distal end of the elongate medical device 19 increases, the sphere representative of the lateral force can be transformed into the torus representative of the longitudinal force.

Alternatively, in some embodiments, the sphere 46 can be representative of the amount of longitudinal force exerted on the distal end of the elongate medical device 19 and can increase in size as an amount of lateral force is increased. In some embodiments, the toruses 47, 48, 49 can be representative of the lateral force exerted on the distal end of the elongate medical device 19 and can move proximally along the graphical representation of the elongate medical device 19, as the lateral force increases. For example, FIG. 5A can indicate that a pure longitudinal force is being applied to the distal end of the elongate medical device 19 and FIG. 5D can indicate that a pure lateral force is being applied to the distal end of the elongate medical device 19. Accordingly, FIG. 5B can indicate that a mixed lateral and longitudinal force (e.g., greater amount of longitudinal force than lateral force) is being applied to the distal end of the elongate medical device 19 and FIG. 5B can indicate that a mixed lateral and longitudinal force (e.g., greater amount of lateral force than longitudinal force) is being applied to the distal end of the elongate medical device 19.

In some embodiments, dimensions associated with $s_d$, $t_d$, $t_{d'}$, $t_{d''}$ can be held constant as an amount of longitudinal and/or lateral force applied to the distal end of the elongate medical device 19 change. The amount of longitudinal and/or lateral force can be indicated by force scope 63 and/or data field 68, as described below, for example, with reference to FIG. 6.

In some embodiments, a color of the indicator shapes discussed herein can change in response to an amount of force exerted on the distal end of the elongate medical device 19 exceeding a threshold. In an example, a color scale can be assigned to a range of force. For instance, a color scale ranging from green to red can be assigned to the range of force. In response to an increase in the amount of lateral force and/or longitudinal force exerted on the distal end of the elongate medical device 19, the color of the indicator shape can change from, for example, green, to yellow, to orange, to red, in accordance with the increased amount of force. For example, at 10 grams of force, the color of the indicator shape can transition from green to yellow; at 20 grams of force, the color of the indicator shape can transition from yellow to orange; and at 30 grams of force, the color of the indicator shape can transition from orange to red. As such, a visual indication of the amount of force that is easy to identify can be provided to the physician.

In some embodiments, a binary color scale can be used. For example, for forces below 30 grams of force, the indicator shape can be displayed as green. Alternatively, for forces at/or above 30 grams of force, the indicator shape can be displayed as red, for example. In some embodiments, a selection can be made through input/output mechanisms 18A, as discussed in relation to FIG. 1, to display the indicator shape using a particular color scale. Alternatively, a selection can be made to display the indicator shape without color (e.g., in greyscale) and/or colors other than those referred to herein.

In some embodiments, the graphical representation of force discussed in relation to FIGS. 2A to 5B can be displayed as emanating from the graphical representation of the distal end of the elongate medical device. In some embodiments, the graphical representation of force can be displayed as emanating from an interior portion of the graphical representation of the distal end, such as in FIGS. 3A to 4B. Alternatively, the graphical representation of force can be displayed as emanating from a point distal to the graphical representation of the distal end, such as in FIGS. 2A and 2B.

Figure 6:
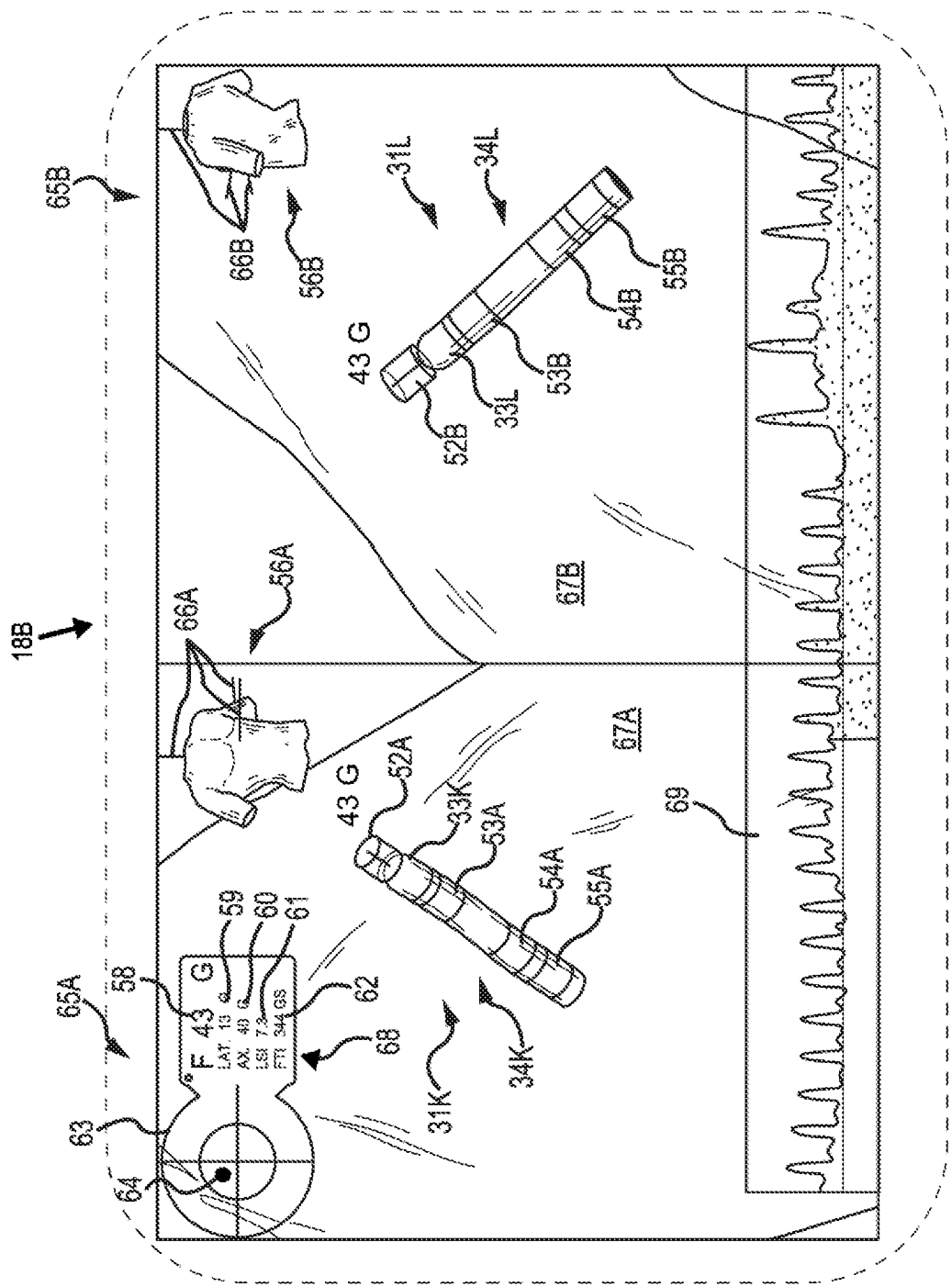
FIG. 6 illustrates a display, in accordance with embodiments of the present disclosure.

FIG. 6 illustrates a display in accordance with embodiments of the present disclosure. The display 18B can be a graphical user interface, as discussed herein. In some embodiments, the display 18B can include a graphical representation of the elongate medical device 31K represented in a first view 65A. In some embodiments, the display 18B can include a graphical representation of the elongate medical device 31L in a second view 65B, which can be from a different perspective than the first view 65A. A perspective associated with the first view 65A and second view 65B can be indicated by perspective indicator 56A and perspective indicator 56B, respectively. For example, first perspective 65A is a perspective from a front quartering angle with respect to a patient's body, which is represented by perspective indicator 56A. The second perspective 65B is a perspective from a rear quartering angle to the patient's body, which is represented by perspective indicator 56B. In some embodiments, the first perspective 65A can display an animation of a first perspective of a heart 67A, while the second perspective 65B can display an animation of a second perspective of a heart 67B.

The perspective indicators can include cross-hairs 66A and 66B that converge on a location within a patient's body where a distal end of the elongate medical device 19 can be located. FIG. 6 illustrates the cross hairs protruding from a torso, however, the cross-hairs can be illustrated as protruding from other portions of a patient's body, dependent on where the elongate medical device 19 is being inserted.

In some embodiments, the first perspective 65A includes a graphical representation of the elongate medical device 31K, which includes an elongate shaft 34K and distal end 33K, along with graphical representation of force 52A (e.g., indicator shape) exerted on the distal end of the elongate medical device 19. In some embodiments, the second perspective 65B includes a graphical representation of the elongate medical device 31L, which includes an elongate shaft 34L and distal end 33L, along with graphical representation of force 52B exerted on the distal end of the elongate medical device 19. In some examples, the graphical representation of the elongate shafts 34K, 34L include electrodes 53A, 54A, 55A, 53B, 54B, 55B, as shown in the first perspective 65A and the second perspective 65B, respectively.

As discussed herein, electrodes and/or sensors (e.g., magnetic sensors) can be placed in the elongate shaft of the elongate medical device 19 for use in determining a position of the elongate shaft. In some embodiments, the electrodes/sensors can be shown in the graphical representation of the elongate shaft 34K, 34L. Accordingly, if the elongate shaft 34K, 34L bends as a result of a lateral and/or longitudinal force being applied to the elongate medical device 19, location information can be received from the electrodes/sensors, which can be used to project a bend in the elongate shaft 34K, 34L displayed on the display 18B.

In some embodiments, the graphical representation of the force (e.g., 52A, 52B) may include a graphical representation of a magnitude of the force, which does not include directional information associated with the force exerted on the distal end of the elongate medical device 19. For example, while a general indication of a lateral and axial force is given, a particular vector from which the force is being exerted is not provided. Such a representation can provide a tool for a physician to quickly look at and interpret. For example, some prior methods have shown a representation of force that also includes a particular vector from which the force is being exerted. In some cases, the most important information a physician may be concerned with is a magnitude of force being exerted against the distal end of the elongate medical device 19 (e.g., to avoid too little or too much exertion of force on the distal end), and not necessarily a particular vector from which the force is being exerted. Presenting additional information may lead to a greater chance of misinterpreting the data. Accordingly, embodiments of the present disclosure can provide a graphical representation of a magnitude of force next to a graphical representation of the distal end 33K, 33L, such that the physician can remain focused on the salient aspects of catheter position and contact simultaneously.

If additional information is desired, a physician can view the bend in the graphical representation of the elongate shaft 34K, 34L, which can generally be used to interpret a particular direction in which the force is being applied to the distal end of the elongate medical device 19. For instance, as discussed herein, the elongate shaft of the elongate medical device 19 can bend in a particular way in response to a force from a particular direction (e.g., lateral, longitudinal) being exerted on a distal end of the elongate medical device 19. The particular bend associated with the elongate shaft can be displayed on the display 18B and used by the physician to determine additional information (e.g., directional force) associated with use of the elongate medical device 19.

In some embodiments, the display can include a force scope 63, which can provide additional information regarding an amount of lateral force and/or longitudinal force being applied to the distal end of the elongate medical device 19. For example, the force scope 63 can include a force blip 64 that is displayed on the force scope 63. In response to an increase in lateral force, the force blip 64 can move to a particular location on the force scope 63, which is indicative of a direction and/or magnitude of the lateral force. Alternatively, in response to an increase in a longitudinal force, the force blip 64 can move to a particular location on the force scope 63, which is indicative of a magnitude of the longitudinal force. In some embodiments, a size of the force blip 64 can change as a result of an increase in magnitude of the lateral force and/or longitudinal force applied to the distal end of the elongate medical device 19. In addition, a color of the force blip 64 can change (e.g., using a color scale) as a result of an increase in magnitude of the lateral force and/or longitudinal force applied to the distal end of the elongate medical device 19.

In some embodiments, the display 18B can include a data field 68, which can display additional data associated with use of the elongated medical device 19. For example, the data field 68 can display a total magnitude of force 58 applied to a distal end of the elongate medical device 19. The total magnitude of force 58 can include a sum of a magnitude of lateral force 59 and a sum of a magnitude of longitudinal force (e.g., axial) 60. In addition, the data field 68 can include a force time integral (FTI) 62 or lesion size index (LSI) 61. The force time integral 62 and the lesion size index 61 can both be calculated and displayed in the data field 68 to assist a physician with determination of size of a lesion created during an ablation procedure.

In some embodiments, a total magnitude of force can be displayed next to the graphical representation of force 52A. For example, as depicted in FIG. 6, a magnitude of force of 43 grams (43 G) can be displayed next to the graphical representation of force 52A. By displaying the magnitude of force next to the graphical representation of force 52A, a physician can view the graphical representation of force 52A, while at the same time maintaining a view of the graphical representation of force 52A. In some embodiments, the total magnitude of force can move with the graphical representation of force 52A. For example, if a diameter or length of the graphical representation of force 52A changes, the magnitude of force can be moved proximally, distally, and/or laterally with respect to the elongate shaft 34K. This can enable the physician to maintain eye contact with the graphical representation of force 52A and the magnitude of force simultaneously.

In some embodiments, the display 18B can include a stability indicator. The stability indicator can indicate whether contact force is steady over time. In an example, heart beat and respiration can cause a variance in contact force over time and can be accounted for through use of the stability indicator. For example, a threshold can be set that includes a particular force. If the force exerted on the distal end of the elongate medical device 19 (e.g., total force, longitudinal force, lateral force) is maintained within the threshold, the stability indicator can provide an indication that contact force is steady over time. As such, an indication can be provided of whether contact between the distal tip of the elongate medical device 19 and tissue 13 is steady.

In an example, the stability indicator can be provided in the data field 68 as a numerical representation. Alternatively, the stability indicator can be represented by changing a color of the force blip 64 and/or a color of a number being displayed in the data field 68. For example, the numerical representation of the total magnitude of force 58 can be displayed as green in response to the contact force being steady over time and can be displayed as red in response to the contact force not being steady over time.

In some embodiments, the data field 68 can include angle information associated with a force being exerted on the distal end of the elongate medical device 19. In an example, the angle information can provide an angle at which a force vector is being exerted on the distal end of the elongate medical device 19. For example, if a force is a pure longitudinal force, an angle of 0 degrees may be displayed. Alternatively, if a force is a mixed longitudinal and lateral force, an angle of 45 degrees may be displayed, for example. Such information can be helpful to a physician in determining that adequate contact is being made between the distal end of the elongate medical device 19 and the tissue 13.

In some embodiments, the display 18B can include a graph 69, which can be used to display additional information about the force being exerted on the distal end of the elongate medical device 19. For example, the graph can include a total amount of force along a y-axis and time along an x-axis. Features of the graph (e.g., scale, color) as well as graphs that include different data (e.g., force time integral, lesion size index) can be selected through user input/output mechanisms 18A.

As discussed in relation to FIG. 1, display 18B can be part of the system 10, which includes instructions stored on the memory 17 and executable by the processing resource 16 for force imaging. In an example, the instructions can be executable to determine an amount of longitudinal force and an amount of lateral force exerted on a distal end of an elongate medical device, as discussed herein. In an example, separate longitudinal and lateral components of force can be determined.

In some embodiments, instructions can be executable to display a graphical representation of the amount of longitudinal force and the amount of lateral force via an indicator shape (e.g., 52A, 52B) next to a distal end of a graphical representation of the distal end 33K of the elongate medical device 31K. With reference to FIG. 4A, the indicator shape 42 can have a fixed proximal diameter ($p_d$), a variable distal diameter ($d_d$), and a variable longitudinal length ($l_l$) length between the fixed proximal diameter and the variable distal diameter.

Instructions can be executed to change the variable longitudinal length between the fixed proximal diameter and the variable distal diameter in response to a change in the amount of longitudinal force being exerted on the distal end of the elongate medical device 19. In an example, the variable longitudinal length can be increased as longitudinal force is increased and decreased as the longitudinal force is decreased. In addition, instructions can be executed to change the variable distal diameter in response to a change in the amount of lateral force being exerted on the distal end of the elongate medical device 19. In an example, the variable distal diameter can increase as lateral force is increased and decrease as lateral force is decreased. As such, the indicator shape can be displayed as a cylinder in response to exertion of a pure longitudinal force being exerted on the distal end of the elongate medical device. For example, the fixed proximal diameter and the variable distal diameter can be a same diameter in response to a pure longitudinal force being exerted on the distal end of the elongate medical device. Alternatively, the indicator shape can be displayed as a disk in response to exertion of a pure lateral force being exerted on the distal end of the elongate medical device. For example, the length between the fixed proximal diameter and the variable distal diameter can be zero in response to a pure lateral force being exerted on the distal end of the elongate medical device.

Figure 7:
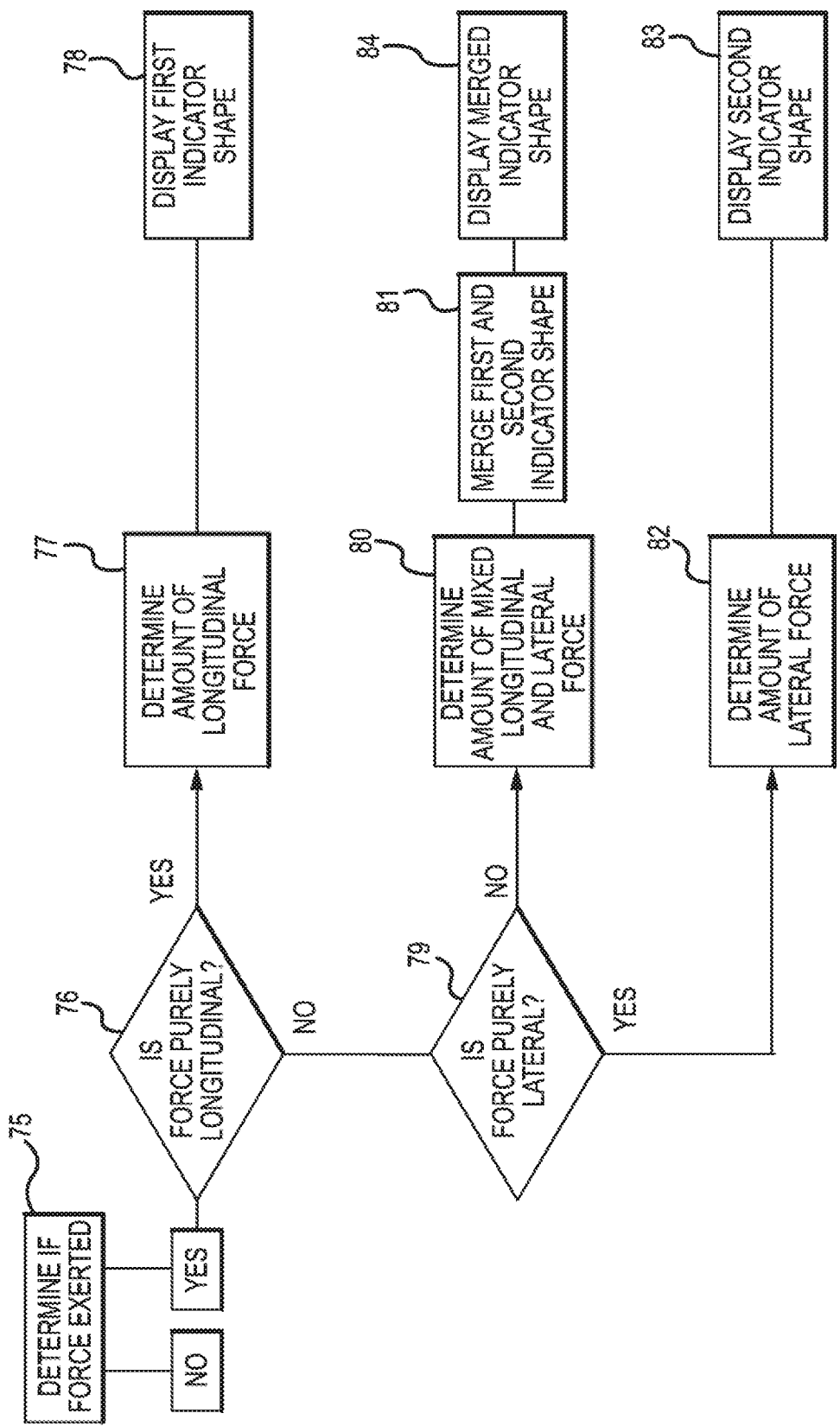
FIG. 7 illustrates a flow chart associated with a method for depicting force, in accordance with embodiments of the present disclosure.

FIG. 7 illustrates a flow chart associated with a method for depicting force, in accordance with embodiments of the present disclosure. The method can include determining, at block 75, if force is exerted on the distal end of the elongate medical device 19. If no force is exerted, or if the force does not meet a minimum threshold, the method can end. However, if a determination is made that a force is exerted on the distal end of the elongate medical device 19, the method can proceed to block 76, where a determination is made of whether the force is purely longitudinal. If the force is purely longitudinal, the method can proceed to block 77, where an amount of longitudinal force applied to the distal end of the elongate medical device 19 is determined. As discussed herein, a graphical representation of the longitudinal force (e.g., indicator shape) exerted on the distal end of the elongate medical device 19 can be displayed next to a graphical representation of a distal end of the elongate medical device, at block 78.

If a determination is made that the force is not purely longitudinal, the method can proceed to block 79, where a determination is made of whether the force is purely lateral. If the force is determined to be purely lateral, the method can proceed to block 82, where an amount of lateral force applied to the distal end of the elongate medical device 19 is determined. Upon determination of the amount of lateral force, a graphical representation of the lateral force (e.g., indicator shape) exerted on the distal end of the elongate medical device 19 can be displayed next to a graphical representation of the elongate medical device, at block 83.

Alternatively, if a determination is made that the force is not purely lateral, a determination can be made that the force is a mixed lateral and longitudinal force being applied to the distal end of the elongate medical device 19. An amount of the lateral force and an amount of the longitudinal force applied to the distal end of the elongate medical device 19 can be determined at block 80. As discussed herein, the graphical representation of the longitudinal force (e.g., first indicator shape) can be merged with the graphical representation of the lateral force (e.g., second indicator shape), at block 81. Accordingly, a cylinder can be merged with a disk and/or a sphere can be merged with a torus, as discussed herein. At block 84, the merged graphical representation of the longitudinal force (e.g., merged indicator shape) can be displayed.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of depicting force has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for depicting force, the method comprising the following:
    determining a force exerted on a distal end of an elongate medical device;
    computing, with a computing device, a graphical representation of the force exerted on the distal end of the elongate medical device, wherein the graphical representation of the force is a first type of indicator shape for a pure longitudinal force exerted on the distal end of the elongate medical device and a second type of indicator shape for a pure lateral force exerted on the distal end of the elongate medical device;
    displaying the graphical representation of the force exerted on the distal end of the elongate medical device next to a graphical representation of the elongate medical device; and
    merging the first type of indicator shape with the second type of indicator shape in response to both an amount of longitudinal force and an amount of lateral force being exerted on the distal end of the elongate medical device.

2. The method of claim 1, further comprising determining the amount of longitudinal force exerted on the distal end of the elongate medical device and the amount of lateral force exerted on the distal end of the elongate medical device.

3. The method of claim 2, further comprising transforming the first type of indicator shape into the second type of indicator shape as the amount of longitudinal force decreases and the amount of lateral force increases.

4. The method of claim 1, wherein:
    the first type of indicator shape is a sphere located at a distal tip of the distal end of the elongate medical device; and
    the second type of indicator shape is a torus located proximally from the distal tip of the distal end of the elongate medical device and is coaxial with the distal end of the elongate medical device.

5. The method of claim 4, wherein a diameter of the sphere is increased in response to an increase in an amount of lateral force exerted on the distal end of the elongate medical device.

6. The method of claim 4, wherein a position of the torus along the elongate medical device is indicative of an amount of longitudinal force applied to the distal end of the elongate medical device.

7. The method of claim 6, wherein the position of the torus along the elongate medical device is moved proximally in response to an increase in an amount of longitudinal force applied to the distal end of the elongate medical device.

8. The method of claim 7, wherein the position of the torus along the elongate medical device is moved distally in response to a decrease in an amount of longitudinal force applied to the distal end of the elongate medical device.

9. The method of claim 1, wherein:
the first type of indicator shape is a cylinder that extends from a distal end of the elongate medical device along an axis defined by the elongate medical device; and
the second type of indicator shape is a disk.

10. The method of claim 9, further comprising increasing a diameter of the disk in response to an increasing amount of lateral force being exerted on the distal end of the elongate medical device.

11. A system for force imaging, comprising the following:
a computing device comprising processor resources and memory resources, the memory resources storing computer-readable instructions that, when executed by the processor resources, cause the processor resources to:
determine an amount of longitudinal force and an amount of lateral force exerted on a distal end of an elongate medical device;
display a graphical representation of the amount of longitudinal force and the amount of lateral force via an indicator shape next to a graphical representation of the distal end of the elongate medical device, wherein the indicator shape has a fixed proximal diameter, a variable distal diameter, and a variable length between the fixed proximal diameter and the variable distal diameter along an axis of the elongate medical device;
change the variable length between the fixed proximal diameter and the variable distal diameter in response to a change in the amount of longitudinal force being exerted on the distal end of the elongate medical device; and
change the variable distal diameter in response to a change in the amount of lateral force being exerted on the distal end of the elongate medical device.

12. The system of claim 11, wherein the indicator shape is displayed as a disk in response to exertion of a pure lateral force being exerted on the distal end of the elongate medical device.

13. The system of claim 11, wherein the fixed proximal diameter and the variable distal diameter are a same diameter in response to a pure longitudinal force being exerted on the distal end of the elongate medical device.

14. The system of claim 11, wherein the length between the fixed proximal diameter and the variable distal diameter is zero in response to the pure lateral force being exerted on the distal end of the elongate medical device.

15. A method for depicting force, the method comprising the following:
determining a force exerted on a distal end of an elongate medical device;
computing, with a computing device, a graphical representation of the force exerted on the distal end of the elongate medical device, wherein the graphical representation of the force is a first type of indicator shape for a pure longitudinal force exerted on the distal end of the elongate medical device and a second type of indicator shape for a pure lateral force exerted on the distal end of the elongate medical device;
displaying the graphical representation of the force exerted on the distal end of the elongate medical device next to a graphical representation of the elongate medical device;
causing a size of the first type of indicator shape to change in response to an increase in the pure longitudinal force; and
causing a size of the second type of indicator shape to change in response to an increase in the pure lateral force.

16. The method of claim 15, further comprising determining an amount of longitudinal force exerted on the distal end of the elongate medical device and an amount of lateral force exerted on the distal end of the elongate medical device.

17. The method of claim 16, further comprising transforming the first type of indicator shape into the second type of indicator shape as the amount of longitudinal force decreases and the amount of lateral force increases.

18. The method of claim 15, wherein:
the first type of indicator shape is a sphere located at a distal tip of the distal end of the elongate medical device; and
the second type of indicator shape is a torus located proximally from the distal tip of the distal end of the elongate medical device and is coaxial with the distal end of the elongate medical device.

19. The method of claim 15, wherein:
the first type of indicator shape is a cylinder that extends from a distal end of the elongate medical device along an axis defined by the elongate medical device; and
the second type of indicator shape is a disk.

20. The method of claim 15, further comprising merging the first type of indicator shape with the second type of indicator shape in response to both an amount of longitudinal force and an amount of lateral force being exerted on the distal end of the elongate medical device.

\* \* \* \* \*